United States Patent [19]

Carter

[11] Patent Number: 5,002,044

[45] Date of Patent: Mar. 26, 1991

[54] DEROTATION WRIST BRACE

[76] Inventor: Peter R. Carter, 3707 Gaston Ave., Suite 520, Dallas, Tex. 75246

[21] Appl. No.: 418,575

[22] Filed: Oct. 10, 1989

[51] Int. Cl.⁵ .......................... A61F 5/10; A61F 5/00; A61F 5/04; A61F 2/58
[52] U.S. Cl. ....................................... 128/77; 623/61; 623/62; 623/39; 128/84 R; 128/87 R; 128/88; 128/80 C
[58] Field of Search ............... 128/77, 80 C, 80 F, 128/84 R, 87 R, 88; 623/61, 62, 39

[56] References Cited

U.S. PATENT DOCUMENTS

| | | | |
|---|---|---|---|
| 2,532,955 | 12/1950 | Shook | 128/80 F |
| 2,832,334 | 4/1958 | Whitelaw | 128/77 X |
| 3,707,963 | 1/1973 | Keropian | 128/77 |
| 4,233,967 | 11/1980 | Daniell, Jr. | 128/87 R X |
| 4,320,747 | 3/1982 | Daniell, Jr. | 623/39 X |
| 4,340,041 | 7/1982 | Frank | 128/80 C |
| 4,353,361 | 10/1982 | Foster | 623/39 X |
| 4,397,308 | 8/1983 | Hepburn | 128/88 |
| 4,508,111 | 4/1985 | Hepburn | 128/87 |
| 4,531,515 | 7/1985 | Rolfes | 128/87 R |
| 4,605,227 | 8/1986 | Hurd et al. | 128/88 X |
| 4,614,181 | 9/1986 | Karlsson | 128/80 C |
| 4,620,532 | 11/1986 | Houswerth | 128/80 |
| 4,655,201 | 4/1987 | Pirmantgen | 623/39 X |
| 4,657,000 | 4/1987 | Hepburn | 128/88 |
| 4,666,158 | 5/1987 | Moro | 128/88 X |
| 4,688,130 | 5/1978 | Applegate | 623/39 X |
| 4,718,665 | 1/1988 | Airy et al. | 128/88 X |
| 4,738,252 | 4/1988 | Friddle et al. | 128/80 C X |
| 4,791,916 | 12/1988 | Paez | 128/80 F X |
| 4,809,688 | 3/1989 | Aymerica del Valle et al. | 128/77 X |
| 4,881,533 | 11/1989 | Teurlings | 128/87 R |

FOREIGN PATENT DOCUMENTS 2526654  11/1983  France .................................. 128/77

Primary Examiner—Richard J. Apley
Assistant Examiner—Linda C. M. Dvorak
Attorney, Agent, or Firm—Richards, Medlock & Andrews

[57] ABSTRACT

A derotation wrist brace providing a volar reduction force and allowing early movement of the radiocarpal joint is provided. A first pair of struts are attached to a forearm support member at their first ends. The second ends of the first struts are attached to a first rotation plate. A second pair of struts are attached to a hand support member at their first ends. The second ends of the second struts are attached to a second rotation plate. The first rotation plates and the second rotation plates are coaxially mounted on a pair of shafts.

16 Claims, 2 Drawing Sheets

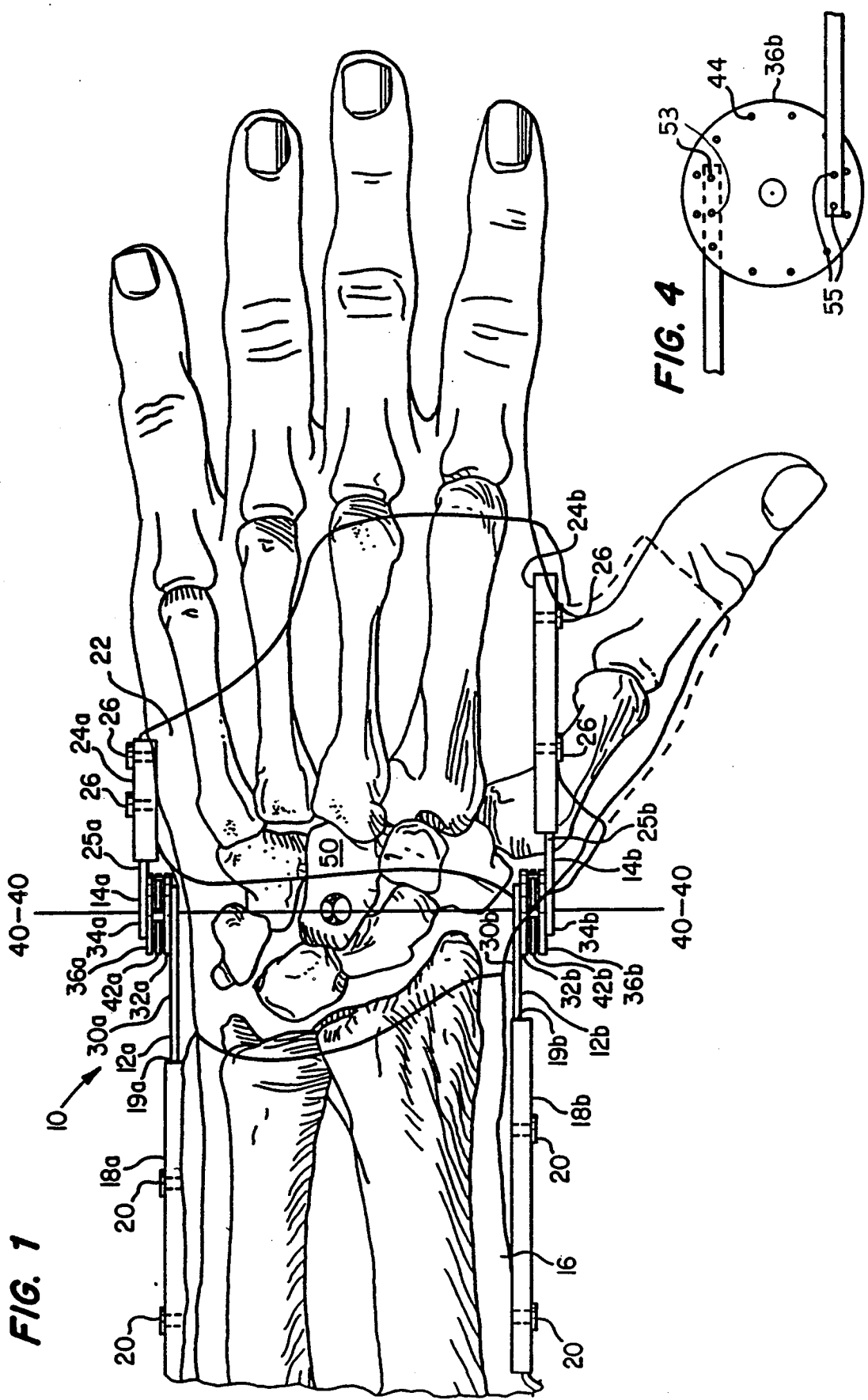

5,002,044

DEROTATION WRIST BRACE

FIELD OF THE INVENTION

This invention relates to a derotation wrist brace for use in rehabilitation of the wrist, and is particularly directed to a derotation wrist brace capable of applying a continuous volar force to the hand.

BACKGROUND OF THE INVENTION

The use of external braces to provide support to and limit movement of human joints is well known. For example, knee braces have been used extensively in the course of rehabilitation of the knee. Such knee braces have proven to be so successful that they are now used in place of the immobilizing knee casts commonly associated with knee surgery. The resulting advancement in the rehabilitation of knee injuries is directly related to the realization that early active motion of a joint following reconstructive surgery is essential to an expedited and complete healing process.

Distal radial fractures are the most common fracture occurring in humans, with frequency estimates ranging as high as 350,000 or more per year in the United States alone. Many physicians find that patients suffering from distal radial fractures ar subjected to a persistent disability which lingers despite the healing of the radius. This disability is related to a failure to restore a normal anatomical orientation between the carpus bones and the radial bone. It is necessary that the fracture be subjected to an accurate and continuous reduction force. Further, early active motion of the radiocarpal joint is desirable in order to expedite the healing process.

SUMMARY OF THE INVENTION

The derotation wrist brace of the present invention includes a pair of first struts and a pair of second struts. The first struts are attached at their first ends to a forearm support member constructed to be fitted about the forearm. The first ends of the second struts are attached to a hand support member. The second ends of the first struts and the second ends of the second supports are attached to brace joints. Each brace joint includes a first rotation plate, a second rotation plate, a shaft, and a limiting blade. Pin holes are formed through the first and second rotation plates such that a pin inserted therethrough will engage the limiting blade in order to restrict the range of motion of the wrist.

BRIEF DESCRIPTION OF THE DRAWINGS

A more complete understanding of the present invention and its advantages will be apparent from the following detailed description read in conjunction with the accompanying drawings, in which:

FIG. 1 is an overall plan view of the derotation wrist brace of the present invention.

FIG. 4 is an elevational view of the brace joint of the present invention in a reduced position.

DETAILED DESCRIPTION

Figure 3:
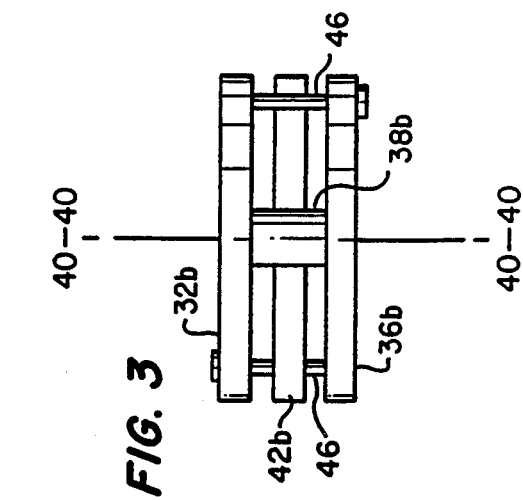
FIG. 3 is an enlarged top view of a brace joint of the present invention.

A derotation wrist brace for use in conjunction with the treatment of wrist injuries, including distal radial fractures, is generally indicated at 10 of FIG. 1. In the preferred embodiment depicted in the accompanying figures, derotation wrist brace 10 includes a set of first struts 12a, 12b, and a set of second struts 14a, 14b. It is to be appreciated that brace 10 can be constructed using a single first strut and a single second strut. However, brace 10 will be described herein with respect to the preferred embodiment in which struts are mounted on both sides of the device. A forearm support member 16 is dimensioned and constructed to be fitted about the forearm. Forearm support member 16 can be constructed of a rigid material such as plastic or, in the alternative, can be constructed of a flexible material. Strut retaining sleeves 18a, 18b are mounted on forearm support member 16. Sleeves 18a, 18b are constructed to receive first ends 19a, 19b of first struts 12a, 12b, respectively. When the desired placement of brace 10 has been achieved, first struts 12a, 12b can be secured within sleeves 18a, 18b through the use of set screws 20.

Hand support member 22 is constructed and dimensioned to be fitted about the hand. Hand support member 22 can be constructed of a rigid or flexible material. Retaining sleeves 24a, 24b are mounted on hand support member 22. Sleeves 24a, 24b are constructed to receive first ends 25a, 25b of second struts 14a, 14b. Struts 14a, 14b can be secured to hand support member 22 through the use of set screws 26.

Second ends 30a, 30b of first struts 12a, 12b are mounted on first rotation plates 32a, 32b, respectively. Second ends 34a, 34b of second struts 14a, 14b are mounted on second rotation plates 36a, 36b, respectively. Rotation plates 32a, 36a are coaxially mounted on shaft 38a such that each is rotatable about axis 40—40. Rotation plates 32b and 36b are coaxially mounted on shaft 38b. Shafts 38a, 38b are preferably coaxially mounted along axis 40—40.

In a preferred embodiment, first struts 12a, 12b are mounted on first rotation plates 32a, 32b, respectively, through the use of two pins 52. Second struts 14a, 14b are mounted on second rotation plates 36a, 36b, respectively, by two pins 54. Pins 52, 54 are preferably mounted through the struts and rotation plates such that pins 52, 54 are equidistant from shafts 38. In another embodiment, pins 52 comprise a pin and a screw wherein the screw can be threadably secured to the first rotation plate in order to secure the first strut thereto. In this embodiment, pins 54 also comprise a pin and a screw. In order to facilitate placement of second pin 52 and second pin 54, preformed holes 53, 55 are formed through first rotation plates and second rotation plates 36, respectively. It will be appreciated that as rotation plates 32a, 32b, 36a, 36b rotate, the hand will be allowed to pivot relative to the forearm about axis 40—40 and, as discussed below, about the os capitatim bone. Also in the preferred embodiment, pins 52, 54 are removable in order to facilitate placement of brace 10 on the wrist.

Rotation-limiting blades 42a, 42b are mounted on shafts 38a, 38b, respectively, between the first and second rotation plates. First rotation plates 32a, 32b and second rotation plates 36a, 36b have a plurality of pin holes 44 formed therethrough, as best seen in FIG. 4. Pin holes 44 are dimensioned to receive pins 46. In use, pins 46 engage limiting blades 42a, 42b when a predetermined degree of rotation of the hand relative to the forearm is obtained. That is, as the hand is rotated relative to the forearm, rotation plates 36a, 36b will be rotated about shafts 38a, 38b, respectively, until pins 44 come into contact with limiting blades 42a, 42b. It will be appreciated that the degree of rotation permitted by brace 10 can be adjusted by selectively positioning pins 46 in pin holes 44. In this way, a single derotation wrist brace 10 can be used throughout the rehabilitation period for the injured wrist.

In a preferred embodiment of the derotation wrist brace of the present invention, shafts 38a, 38b are constructed of a radiopaque material and are therefore identifiable in an x-ray. In this preferred embodiment, first struts 12a, 12b, second struts 14a, 14b, forearm support member 16, hand support member 22, first rotation plates 32a, 32b, second rotation plates 36a, 36b, and limiting blades 42a, 42bare constructed of a radiolucent material. In this way, an x-ray of the wrist to which the derotation wrist brace 10 has been applied would show only the orientation of shafts 38a, 38b, and the relative positions of the radius, the ulna, and the carpus bones. It is desirable that axis 40—40 is positioned such that it passes through the os capitatim bone 50 of the carpus. The os capitatim has been determined to be the center of rotation for the wrist.

Figure 6:
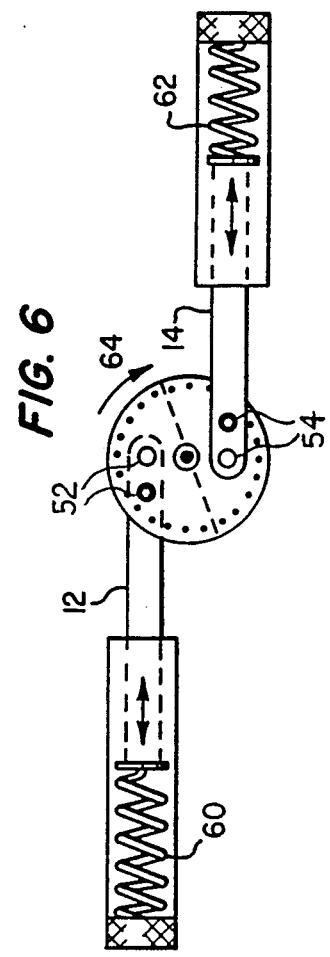
FIG. 6 is an elevational view of an alternative embodiment of the brace joint of the present invention.

In the alternative embodiment depicted in FIG. 6, compression springs 60 are disposed within sleeves 18a, 18b in order to apply an active force to first struts 12a, 12b. In this embodiment, struts 12a, 12b are slidably mounted within sleeves 18a, 18b. Also in this alternative embodiment, tension springs 62 are disposed within sleeves 24a, 24b and create an active force against second struts 14a, 14b. It is to be appreciated that tension springs can be used in place of compression springs 60, 62 without departing from the scope of this alternative embodiment of the present invention. Due to the action of compression springs 60, 62, an active force is imparted by brace 10 to the wrist in the direction indicated by arrows 64. Due to the configuration of brace 10, an active volar reduction force is imparted in this alternative embodiment. An active volar translocation force can be imparted by replacing compression springs 60, 62 with tension springs.

The derotation wrist brace of the present invention is applied to the wrist by placing forearm support member 16 about the forearm and hand support member 22 about the hand of the patient. In order to allow the proper orientation of axis 40—40, first struts 12a, 12b and second struts 14a, 14b are not secured in sleeves 18 and 24, respectively, at this juncture. Through the use of x-ray equipment, axis 40—40 is positioned such that it passes through the os capitatim bone 50 of the carpus. Only at this point are screws 20 tightened, thereby securing first struts 12a, 12b in sleeves 18a, 18b. Screws 26 are also tightened at this time, thereby retaining second struts 14a, 14b in sleeves 24a, 24b. In this way, the lengths of first struts 12a, 12b and second struts 14a, 14b can be effectively adjusted to each patient. In addition, this method ensures the physician that axis 40—40 is properly oriented through the os capitatim, the center of rotation of the hand relative to the forearm.

Figure 5:
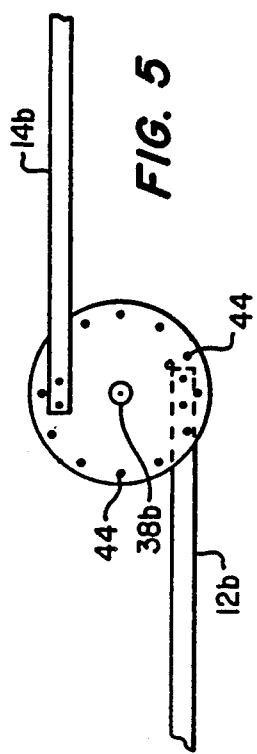
FIG. 5 is an elevational view of the brace joint of the present invention prior to rotation of the joint to the reduced position.
Figure 2:
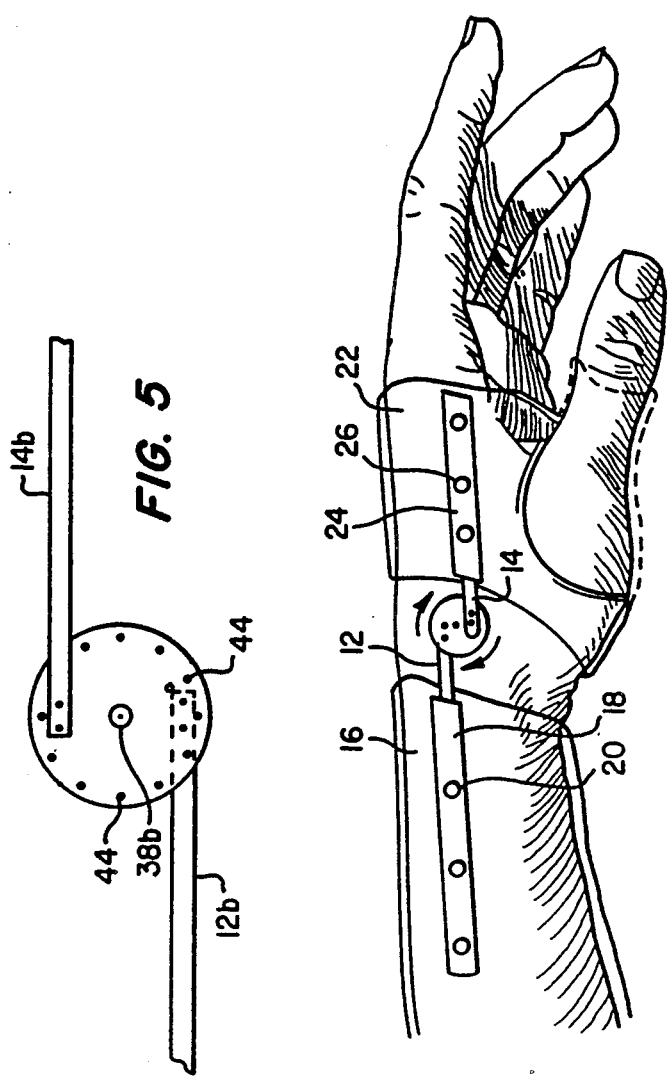
FIG. 2 is a side elevational view of the derotation wrist brace of the present invention.

Due to the translocation of the carpal bones commonly associated with fractures of the distal radius, the relative orientation at this point in the process of second struts 14a, 14b with respect to first struts 12a, 12b will be substantially as depicted in FIG. 5. A reduction force must be applied to the carpal bones in order to restore their normal anatomical configurations. The application of a reduction force causes the hand to be moved downwardly relative to the forearm, and thus also causes second rotation plates 36a, 36b to be rotated to the position shown in FIG. 4. In order to facilitate application of a reduction force to the carpus bones, only one pin 52 and one pin 54 are used to connect struts 12, 14 to rotation plates 32, 36, thereby allowing greater mobility of the hand during application of the reduction force. However, when struts 12, 14 reach the positions depicted in FIG. 4, a second pin 52 and a second pin 54 are placed through the struts rotation plates. In this way, the mobility of the hand is limited, relative to the forearm, to rotation about axis 40—40.

It will be appreciated that the volar reduction force created by the relative orientation of second struts 14a, 14b and first struts 12a, 12b is maintained despite the fact that brace 10 allows for flexion and extension of the hand relative to the forearm. In this way, the derotation wrist brace of the present invention provides a continuous volar reduction force while still providing for early movement of the radiocarpal joint. It will also be appreciated that the derotation wrist brace of the present invention can be used to apply a continuous volar translocation force. Such a force would be desirable where an injury to the wrist forced the hand ventrally relative to the wrist. In this instance, FIG. 4 would represent the state of the brace prior to the application of a connecting force. The brace would then be rotated and locked in the position depicted in FIG. 5 in order to provide a continuous volar translocation force.

Although the derotation wrist brace of the present invention has been described in detail with respect to preferred embodiments, it will be appreciated that various changes and alterations may be made without departing from the true spirit and scope of the present invention.

WHAT IS CLAIMED IS:

1. A derotation wrist brace comprising:
    a first strut having a first end and a second end;
    a forearm support member dimensioned to fit about a forearm, said first end of said first strut mounted on said forearm support member;
    a second strut having a first end and a second end;
    a hand support member dimensioned to fit about a hand, said first end of said second strut mounted on said hand support member;
    a rotational brace joint comprising a first rotation plate, a second rotation plate, a shaft, and a limiting blade, said first rotation plate and said second rotation plate having a plurality of pin holes formed therethrough, said second end of said first strut mounted on said first rotation plate and said second end of said second strut mounted on said second rotation plate, said shaft having a first end and a second end, said first rotation plate mounted on said first end of said shaft and said second rotation plate mounted on said second end of said shaft, said limiting blade mounted on said shaft between said first rotation plate and said second rotation plate; and
    a pin dimensioned for insertion through said pin holes formed through said first and said second rotation plates whereby said pin engages said limiting blade upon rotation of said rotation plates.

2. The derotation wrist brace of claim 1 wherein said second end of said first strut is mounted on said first rotation plate through a pair of pins mounted through said first strut and said first rotation plate, said pins being positioned on said first rotation plates such that said pins are equidistant from said shaft.

3. The derotation wrist brace of claim 1 wherein said second end of said second strut is mounted on said second rotation plate through a pair of pins mounted through said second strut and said second rotation plate, said pins being positioned on said first rotation plate such that said pins are equidistant from said shaft.

4. A derotation wrist brace comprising:
   a pair of first struts, each of said first struts having a first end and a second end;
   a forearm support member dimensioned to fit about a forearm, said first ends of said first struts being mounted on said forearm support member;
   a pair of second struts, each of said second struts having a first end and a second end;
   a hand support member dimensioned to fit about a hand, said first ends of said second struts being mounted on said hand support member; and
   a pair of rotational brace joints, each of said brace joints comprising a first rotation plate, a second rotation plate, and a shaft, said second ends of said first struts mounted on said first rotation plates and said second ends of said second struts mounted on said second rotation plates, each of said shafts having a first end and a second end, said first rotation plates rotatably mounted on said first ends of said shafts and said second rotation plates rotatably mounted on said second ends of said shafts.

5. The derotation wrist brace of claim 4 wherein each of said shafts is constructed of a radiopaque material whereby said shaft is identifiable in an X-ray.

6. The derotation wrist brace of claim 5 wherein said first struts, said second struts, said forearm support member, said hand support member, said first rotation plate, and said second rotation plate are constructed of a radiolucent material whereby they are invisible to an x-ray.

7. The derotation wrist brace of claim 4 wherein said second ends of said first struts are mounted on said first rotation plates through a pair of pins mounted through said first struts and said rotation plates, said pins being positioned on said rotation plates such that said pins are equidistant from said shafts.

8. The derotation wrist brace of claim 4 wherein said second ends of said second struts are mounted on said second rotation plates through a pair of pins mounted through said second struts and said rotation plates, said pins being positioned on said rotation plates such that said pins are equidistant from said shafts.

9. The derotation wrist brace of claim 4 further comprising a rotation-limiting blade, said rotation-limiting blade mounted on one of said shafts whereby said rotation-limiting blade restricts the degree of rotation of said wrist brace.

10. The derotation wrist brace of claim 9 wherein said first rotation plates and said second rotation plates have a plurality of pin holes formed therethrough, said brace further comprising a pin dimensioned for insertion through said pin holes whereby said pin engages said rotation-limiting blade upon rotation of said brace, thereby restricting the degree of rotation of said wrist brace.

11. The derotation wrist brace of claim 9 wherein a rotation-limiting blade is mounted on each of said shafts.

12. The derotation wrist brace of claim 4 wherein said shafts are coaxially oriented such that said wrist brace is rotatable about a single axis.

13. A derotation wrist brace comprising:
    a pair of first struts, each of said first struts having a first end and a second end;
    a forearm support member dimensioned to fit about a forearm, said first ends of said first struts being mounted on said forearm support member;
    a pair of second struts, each of said second struts having a first end and a second end;
    a hand support member dimensioned to fit about a hand, said first ends of said second struts being mounted on said hand support member;
    a pair of rotational brace joints, each of said brace joints comprising a first rotation plate, a second rotation plate, a shaft, and a limiting blade, said first rotation plate and said second rotation plate having a plurality of pin holes formed therethrough, said second ends of said first struts mounted on said first rotation plates and said second ends of said second struts mounted on said second rotation plates, each of said shafts having a first end and a second end, said first rotation plates rotatably mounted on said first ends of said shafts and said second rotation plates rotatably mounted on said second ends of said shafts, said limiting blades being mounted on said shafts; and
    a pin dimensioned for insertion through said pin holes formed through said first and said second rotation plates whereby said pin engages said limiting blade upon rotation of said rotation plates, thereby limiting the degree of rotation of said first and said second rotation plates relative to one another.

14. A method for applying a derotation wrist brace to a wrist having a forearm support member, a hand support member, a pair of first struts, a pair of second struts, a pair of first rotation plates, and a pair of second rotation plates, comprising:
    placing said forearm support member of said derotation wrist brace about the forearm;
    placing said hand support member of said derotation wrist brace about the hand;
    securing said pair of first struts of said derotation wrist brace to said forearm support member of said derotation wrist brace;
    securing said pair of second struts of said derotation wrist brace to said hand support member of said derotation wrist brace;
    applying a reduction force to the hand, thereby forcing the hand downwardly with respect to the wrist;
    securing said second struts to said second rotation plate of said derotation wrist brace, thereby creating a continuous volar reduction force; and
    inserting pins into preselected pin holes formed through said first and said second rotation plates of said derotation wrist brace.

15. The method for applying a derotation wrist brace of claim 14 further comprising aligning a first and a second shaft of said derotation wrist brace along a single axis.

16. The method for applying a derotation wrist brace of claim 15 wherein said axis is oriented through the os capitatim of the carpus through the use of an x-ray.

* * * * *